United States Patent [19]

Richard et al.

[11] 4,252,118
[45] Feb. 24, 1981

[54] NON-REUSABLE DRUG PREFILLED SYRINGE ASSEMBLY AND METHOD OF USE

[76] Inventors: Jacques Richard, 42 Rue du Colonel Candelot, Bourg-la-Reine; Claude Imbert, 6 Chemin de la Concorde, La Tronche, both of France

[21] Appl. No.: 789,624

[22] Filed: Apr. 21, 1977

[30] Foreign Application Priority Data

Apr. 23, 1976 [FR] France ............................... 76 12199

[51] Int. Cl.³ .............................................. A61M 5/00
[52] U.S. Cl. ................................. 128/218 P; 128/234
[58] Field of Search ............ 128/215, 218 P, 218 PA, 128/218 N, 218 R, 2 F, DIG. 5, 234

[56] References Cited

U.S. PATENT DOCUMENTS

| 3,045,674 | 7/1962 | Goldberg | 128/218 P |
| 3,118,448 | 1/1964 | Gottschalk | 128/218 N |
| 3,809,082 | 5/1974 | Hurschman | 128/218 P |
| 3,902,491 | 9/1975 | Lajus | 128/218 P |

*Primary Examiner*—John D. Yasko
*Attorney, Agent, or Firm*—Weiser, Stapler & Spivak

[57] ABSTRACT

A non-reusable prefilled syringe for a single administration of a drug solution. The syringe has a plunger for expelling the solution which is detachably fitted with an elastomeric cap. The syringe allows for a pre-vein test but is not adapted for reuse. A method of use for subcutaneous injection of mini-doses of the drug solution.

36 Claims, 7 Drawing Figures

NON-REUSABLE DRUG PREFILLED SYRINGE ASSEMBLY AND METHOD OF USE

Syringe assemblies are known which employ a hollow syringe barrel and a syringe plunger. The plunger includes a rubber stopper portion for sealing engagement with the inner walls of the syringe barrel and a plunger rod connected to the stopper and extending rearwardly from the syringe barrel so that the plunger rod can be reciprocated within the barrel to aspirate or dispense fluids. The stopper is formed of a conventional material such as rubber and the plunger rod is generally formed of plastic material. Various means are employed for interconnecting one to the other. One form includes a threaded reduced end portion on the rod which inter-engages with a corresponding threaded recess in the stopper. Another form employs a reduced tip on the plunger rod terminating in a flanged head. The flanged head and reduced tip are adapted to be received in an accomodating recess in the rubber stopper by snapping into place in conventional fashion. The flange includes a substantial cylindrical portion of wide diameter to provide a wide undercut or lateral wall to facilitate positive interference and guard against disassembly.

Once the plunger has been assembled, it is utilized as an integral assembly and is not designed for use of detachment of the plunger rod from the sealing stopper. Detachment is difficult and requires either an extensive unthreading action in the case of the threaded interengagement or a substantial amount of force in connection with the flanged head arrangement. Even a substantial amount of force may not cause disassembly with the stopper being only held in the syringe band by frictional force.

It would be extremely advantageous to provide a plunger assembly where the rod can be quickly and easily detached from the stopper after single use and disposed of thereby facilitating the provision of a single use syringe assembly. The plunger rod will be destroyed after easy removal from the stopper and there would be no rod available for reuse purposes.

One of the objects of the invention is to provide a syringe for a non-reusable syringe assembly which either precludes or at least makes very difficult the reuse of the syringe.

Another object of the syringe of the invention particularly filled with a drug, especially an isotonic drug, allows for carrying out what is called "the vein test".

Another object of the invention is to provide a syringe which allows for carrying out "the vein test" and then for single use and yet prevent reuse of the syringe.

Another object of the invention is to provide a syringe which, once it has been emptied of its drug content, when an attempt is made to reuse it, the rod detaches itself from the stopper of the assembly (the rod and the stopper detach themselves from each other) without the amount of force which was called for in the syringes of the prior art and without any unscrewing action of the rod from the stopper.

Another object of the syringe of the invention especially when filled with a suitable drug is to provide for measured pre-dosed, mini-doses of drug for dispensing antithrombotic drug particularly heparin, more especially forms of salts of heparin such as sodium and/or calcium salts of heparin.

Another object is to provide an easily dispensable dose of heparin, which would allow under appropriate circumstances a patient to self-administer the drug without necessarily the assistance of trained medical personnel at preselected times prior to surgery, such as several days before.

An important object of the invention is the provision of a prefilled, non-reusable syringe assembly which permits the "vein test", administration to the patient and then essentially precludes reuse of the syringe by the plunger becoming inoperative in that the plunger rod comes off by itself.

Yet another important object of the invention is a non-reusable syringe for a drug which will deliver an exact volume of a predetermined small dose of the drug to a patient without loss in the syringe. The invention is further described in the following Figures, in which FIG. 1 is a side elevation of a syringe of the invention;

DESCRIPTION OF THE PREFERRED EMBODIMENT

Figure 1:
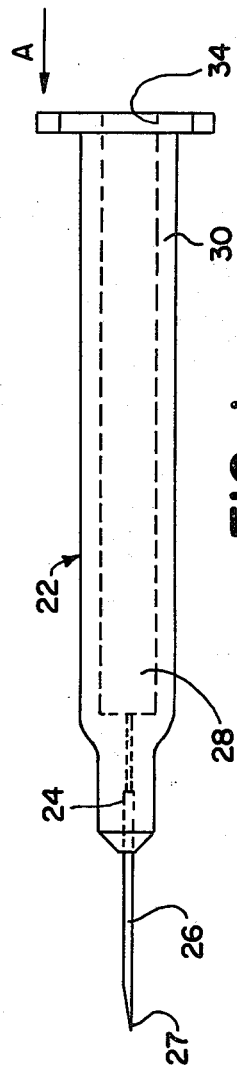
Figure 2:
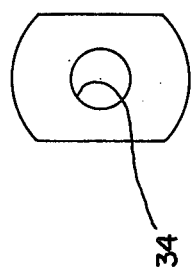
FIG. 2 is an end view along the arrow A of FIG. 1.
Figure 3:
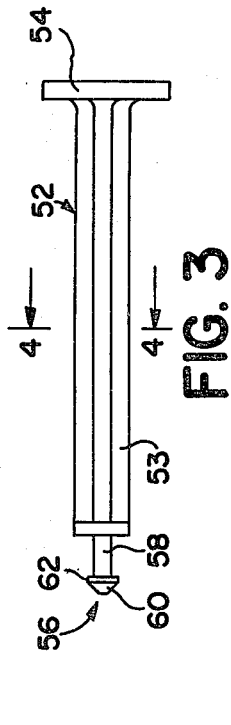
FIG. 3 is a side elevation of the piston-rod of a syringe of the invention.
Figure 4:
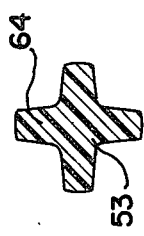
FIG. 4 is a larger scale view in cross-section along line 4—4 of FIG. 3.
Figure 5:
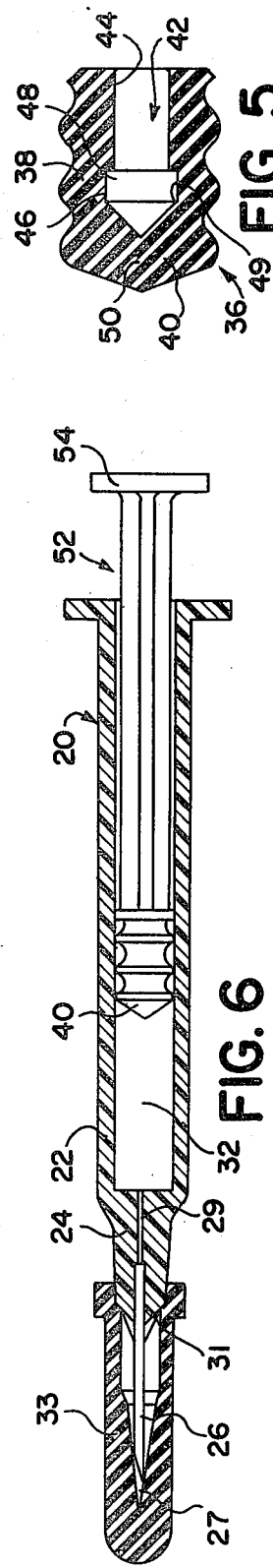
FIG. 5 is a larger scale view in cross-section of the stopper of the invention.
Figure 6:
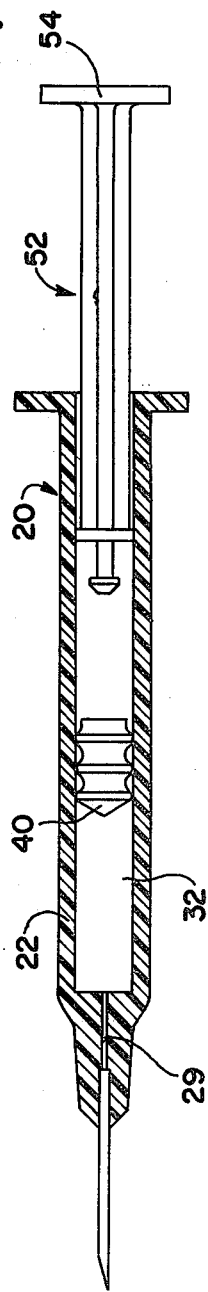
FIG. 6 is a view in partial cross-section of a syringe of the invention before use.

In the illustrated embodiment, there is shown a prefilled non-reusable syringe assembly 20. The assembly includes a syringe barrel 22 having a reduced distal end portion 24 in which is mounted a needle 26 for entry into the patient. The passageway through the needle communicates with the hollow chamber 28 in the main body portion 30 of syringe barrel 22.

Needle 26 is provided with a pointed tip 27 to facilitate its entrance into the patient and a continuous passageway therethrough in communication with a narrow passageway 29 in the syringe barrel which in turn communicates with the chamber 28 in the barrel. Needle 26 is mounted in fixed position into the end portion 24 which terminates, preferably in a somewhat pointed, yet smooth fashion. The provision of the fixed needle so mounted is best adapted for contact with the vein of the patient to be essentially air and leak-proof, so that there is no loss of drug when injecting the patient. The needle is fixed into the glass by means of a plastic, such as a known epoxy, which can be sterilized. Needle 26 is protected prior to use by means of a plastic or rubber sheath 33 which can be seated on the reduced tip 24 of the syringe barrel in frictional engagement therewith and removed just prior to use.

A predetermined dosage of medicament 32 is introduced into the syringe barrel through the open proximal end 34 of the syringe barrel and is sealed in position by means of a self-sealing elastomeric stopper 36. The stopper can be formed of a conventional material such as natural or synthetic rubber and is provided with a plurality of concentric ribs 38 on its outer surface for sealing engagement with the inner walls of the syringe barrel 22. When the plunger is depressed into the cylinder, the seal formed by the ribs prevents escape of the medicament from the cylinder and thereby cause it to be injected into the patient. The number of ribs employed is a matter of choice. Normally, the spaces between the ribs behind space 32 filled with the drug, are free of the drug (empty); they may contain air or partial vacuum.

The forward end 40 of this stopper is closed and the rear end contains recess 42 with the recess having a narrower entrance portion 44 extending into an enlarged flange receiving portion 46. The flange receiving portion is formed with a largest diameter point forming lateral support 48 adjacent narrower portion 44 with the flange portion extending as a cylinder 49 of constant diameter and then tapering inwardly away from narrower portion 44 to a terminal closed end 50.

Stopper 36 is adapted to be interengaged with a plunger rod 52 of a conventional material such as a thermoplastic polystyrene for example, with rod 52 and stopper 36 forming the plunger assembly for use with syringe barrel 22. Rod 52 extends beyond the rear opening 34 in the syringe barrel and has a finger gripping portion 54 at the exposed end for facilitating withdrawal and depression of the plunger assembly with respect to the barrel. A distal projection 56 of the rod 52 has a reduced diameter portion 58 terminating in a flanged tip 60. The projection 56 contains a bended shoulder 62 formed at the point of engagement between the frustoconical tip 60 and the narrower diameter portion 58. Shoulder 62 is a smaller diameter than the diameter of the undercut on stopper 36 so as to provide some interference therebetween when attached but also facilitating disassembly with a predetermined axial force is applied.

In this manner the plunger rod can be inserted within the stopper and the resilient stopper will be displaced to permit shoulder 62 to seat on the shoulder formed by the base of the flanged recess 46 in the stopper, thereby holding the stopper to the rod. The projection 56 carries stopper 36 of the rod with which it cooperates to effectuate the release.

The intermediate body portion 53 of the plunger rod has, optionally, a plurality of longitudinal ribs 64 for adding rigidity and strength to the plunger rod 52.

An example of the embodiment illustrated in FIG. 1 can include the following dimensions. The barrel of the syringe has a diameter of 5 mm; and body 53 has a diameter of 4 mm; and projection 56 a length of 4.5 mm so that the length of the stem body is 53 mm including the finger gripping portion 54. The diameter of the projection is 2 mm.

In operation, the syringe is filled with the appropriate dosage of medicament 32 and the assembled rod 52 and stopper 36 are positioned in the syringe barrel with the finger gripping end 54 projecting from the rear end of the syringe barrel. The assembly is sterilized. For injection into a patient, sheath 33 is removed from the needle and the needle 26 is inserted into the patient. Before use a slight rearward pressure on the plunger is applied to aspirate and make sure that the needle is not improperly placed in the patient; this being what is called "the vein test".

It is an aspect of the prefilled syringe of the invention that it allows for carrying out the "vein test" which necessitates the limited withdrawal of the plunger within the barrel, this without the stopper coming off from the rod. By limited withdrawal is meant that withdrawal which is necessary to draw some fluid from the patient while the syringe contains the drug solution it is capable of the vein test, which requires withdrawal of the plunger within the barrel but without the stopper coming off the rod, and then after the injection has been given, will allow the stopper and the rod to become disconnected from each other as the plunger rod is withdrawn inside the barrel. The syringe of the invention allows for a preselected withdrawal of the rod without disassembly of the rod and stopper. After determination of the presence or absence of blood in the needle (which would indicate the proper or improper location of the needle) with the needle properly located in the patient as originally inserted or as reinserted, depression of the plunger rod forward into the barrel will dispense the medicament through the communicating needle and into the patient until the dosage has been dispensed. Thereafter, withdrawal of the plunger rod, which requires a minimal amount of axial force above that required for aspiration as part of the vein test, will cause a detachment of the rod from the stopper. The detachment of the rod will occur at any time or location within the barrel as the plunger rod is being withdrawn. It is an unexpected aspect of the syringe of the invention that detachment is facilitated by the nature of the interengaging surfaces between projection 56 and recess 42 in the stopper. The interengagement between peripheral base 48 and cooperating shoulder 62 is of a sufficient width to provide the desired amount of friction and yet the withdrawal of the stopper rod is possible with a minimum amount of deformation of the interfering surface on the resilient stopper. Additionally, the frustoconical shape of the remaining portion of the flanged tip from the widest point to the narrowest point at the tip facilitates the ease of withdrawal of the stopper rod since once the widest portion of the rod has past the initial point of interference, the rod becomes narrower toward its distal tip and can be quickly and efficiently removed. The configuration of the flanged tip 60 is designed so that a narrow bended shoulder 62 is formed and then the remainder of the flange is frustoconical in configuration tapering inwardly away from the main body of the plunger rod. This narrowing of diameter after the point of interference facilitates ease of removal of the rod in contrast to a stopper rod which has a large length cylindrical flange of a constant diameter which must bypass a point of interference in the rubber stopper. This feature along with the provision of a minimum diameter lateral should, cooperate to permit the removal of the rod from the stopper with the use of a minimum of additional axial force in excess of that required for aspiration. Additionally, there is only partial surface contact between the tip of the rod and the surfaces forming the flanged portion of the recess in the stopper. This facilitates disengagement therebetween since there is less friction between parts and an empty space or void is present.

Figure 7:
FIG. 7 is a view in partial cross-section of a syringe after use and withdrawal of the rod.

FIG. 7 shows the syringe after use, the drug having been injected, and the rod withdrawn back into the barrel, thus leaving stopper 36 behind in the barrel, detached from projection 56, now exposed in the empty cavity.

If the rod and stopper were not to become disengaged in accordance with the invention, the syringe would be reusable by immersing the syringe into a drug solution and withdrawing the plunger rod within the barrel, thereby by aspiration causing the drug to fill the syringe. If one were to so attempt to refill the syringe of the invention, the stopper comes off the rod, the syringe of the invention is thus self-destructible, if such use were attempted.

Once rod 52 has been separated it can be disposed of. The syringe barrel and stopper are not suitable for reuse.

An alternative form of syringe assembly to which the present invention is also directed includes a syringe barrel containing a predetermined dose of medicament in the hollow interior thereof with a stopper in the barrel sealing one end and a removable cap sealing the other open end of the syringe barrel. In use the cap is removed from the reduced tip open end of the barrel and a needle and hub assembly is interconnected therewith in conventional fashion. A plunger rod as described above is then coupled with the stopper in the syringe barrel and the syringe is operated in the same manner as in the previously discussed embodiment.

Another fact or element which contributes to the self-releasing or safety feature of the syringe assembly of the invention is the density or liquid nature of the medicament within the syringe, usually an isotonic solution. The specific gravity of a salt of heparin for which the syringe is especially well adopted is generally in the order of 1, of calcium heparin commonly in the range of 1.06 to 1.1 g/cm$^3$.

The non-reusable syringe assembly of the invention prefilled with the desired medicament can be used with conventional materials which are normally used in the manufacture of known syringes including the use of conventional lubricants such as silicone.

The self-releasable feature of the rubber cap from the piston rod in the assembly of the invention can be expressed by stating that the force necessary to release the stopper or in other words, the force holding the stopper on the rod, is less than that necessary to aspirate a new solution when the plunger has been depressed in a subsequent attempt to refill the syringe with a fresh solution of a drug by withdrawing the plunger rod within the barrel.

If the rod and stopper were not to become disengaged in accordance with the invention, the syringe would be reusable by immersing the syringe into a drug solution and withdrawing the plunger rod within the barrel, thereby by aspiration causing the drug to fill the syringe. If one were to so attempt to refill the syringe of the invention, the stopper comes off the rod.

Thus, in the stopper of the invention, various other shapes for the recess therein can be contemplated. The recess can be of a configuration conforming substantially to the projection on the rod as in the present embodiment or one which terminates into a point or other similar shape, as long as it provides the desired amount of fractional engagement to the interconnected parts to hold them together when the plunger is depressed to expel the solution and facilitate disconnection when the plunger is pulled back after use. The tip in the recess can be extended to a point or can be arcuate in configuration. The same criteria applies to the tip of the plunger rod. For instance, it need not have a flange (like 62). The tip of the rod is so shaped not to be disengaged from the mating recess and not to be disconnected from the cap when applying the vein test but being disconnected when an attempt at refilling the syringe through the needle is made, as for reuse, after discharge of the drug.

It is to be noted that projection 56 is in accordance with the invention free of threads, a feature which was or has been adopted in previous syringes for rotatably disengaging the plunger from the rubber cap.

The syringe of the invention is particularly well suited for administration of heparin, especially for low-dose (or mini-dose) subcutaneous heparin administration in preventing venous thromboembolic disease.

It is well known that one very important clinical use for heparin is its effectiveness as an antithrombotic agent. Many problems reported in the literature have been encountered in the administration of heparin to patients in need of antithrombotic therapy. Dosage regulation is a critical aspect of therapy including the unit dose, the frequency, duration and other similar aspects. Unsatisfactory results which physicians have reported such as excessive bleeding at the sight of injection, may have been caused by using vials of heparin containing large amounts of units (such as 125,000 IU) of heparin out of which the physician seeks to administer 5,000 IU in a 0.2 ml syringe. There is a serious need for prefilled syringes of the invention with which it is possible to regulate exactly the administration of the drug. The syringes are prefilled with heparin in a form of a salt such as sodium or other salts and particularly calcium, or mixtures of calcium and sodium in preselected proportions and with decreased sodium content. With the syringe of the invention, there can be administered the exact required minidose employing the entire syringe and without loss of the drug.

An important embodiment of the invention is the combination of the non-refillable syringe of the invention filled with minidose of heparin. There are literature reports that minidose heparine has important prophylactic value as an antithrombotic agent.

Another embodiment of the invention therefore is a method for administering minidoses of heparin from the syringe of the invention at preselected times to surgical patients, in particular presurgical administration.

One advantage of minidose administration to surgical patients is the elimination of individual dosage monitoring.

In accordance with the invention there is provided a non-refillable syringe filled with sodium or calcium (or mixture of these salts) of heparin, in low dose suited for subcutaneous heparin injection. Patients treated in this manner are less prone to thrombosis.

Ideally as it appears at this time, the non-refillable syringe is filled with a minidose of heparin, which is about 5,000 IU. In accordance with the method of administration of the invention there is applied, if the clinical circumstances require it, minidoses of 2,500 IU or others going up to about 10,000 IU. A regimen of administration which has been recommended is 10,000 IU of heparin subcutaneously at midnight before surgery, the anticoagulant effect lasting approximately twelve hours. If desired, such as when surgery extends beyond this period, additional heparin, in minidose of about 2,500 IU can be administered sucutaneously during the operation and at the completion of the operation 2,500 IU are additionally administered subcutaneously every six hours until the patient is fully active. Other surgical groups have been given heparin, three doses every twelve hours, of 5,000 IU of heparin subcutaneously starting before surgery and such as 5,000 IU of heparine every twelve hours starting before operation and continuing for five days thereafter.

A standard minidose of heparin particularly well suited for administration in accordance with the invention is 5,000 IU of heparin, administered subcutaneously at preselected times, periodically before surgery then at preselected times during surgery and thereafter until danger of thrombosis has been satisfactorily reduced. The end point where administration is not necessary any more is determined in accordance with well-known methods.

It is to be noted that in certain circumstances, it may be recommended by the physician to have minidoses going as high as 10,000 IU instead of the other doses described above.

In accordance therefore with the invention, there is provided a very satisfactory method, and device for prophilaxis of deep vein thrombosis which is well tolerated by the patients, devoid of side effects, and requires no special monitoring which other non-low dose is apt to require.

The ideal volume of heparin contained in the syringe is 2 ml, if desirable the content of heparin can be increased to 0.4 ml and decreased to a volume of 0.1 ml.

It is to be noted that in accordance with the device and the method of the invention what is called the "vein test" is if desirable, carried out prior to the administration of the heparin. The person administering the heparin can test the syringe to determine if the injection which is about to be given is into a vein which is not desired or subcutaneously which it is. If upon withdraw the needle shows that blood has been sucked in, then obviously the administration is not subcutaneous.

The types of heparin solutions which are injected are solutions of a desirable salt of heparin such as the sodium salt. Even more desired than the sodium salt, is a salt of calcium or a salt of heparin having high proportions of calcium such as about from about 6.0 percent calcium salt, the remainder being other salts as for instance sodium salt. A very highly desirable and presently preferred heparin for dispensing in accordance with the method and in the device of the invention is a calcium salt containing at least about 8.0 percent of calcium, the remainder being sodium. If desired, of course, there may be used forms of heparin which are essentially only calcium heparinate and contain no more than about 1 or less percent of sodium, or another salt.

At this time, the sodium heparin and calcium heparin are by far the preferred salt solutions which are to be administered in accordance with the method and with the syringe of the invention. The calcium salt of heparin has been reported to have particular desirable therapeutic and prophylactic effect in mini-doses, especially for certain applications. Solutions of drugs other than heparin, especially those in isotonic solutions, can also be administered with the syringe and in accordance with the method of the invention.

When not sodium, there may be present other salts, like magnesium.

The ampules-syringes of the invention are prefilled with a concentrated solution of heparin—sodium or calcium—of 25,000 IU/ml which is made up as follows:

To obtain 40 liters of said concentrated solution there is dissolved 1000 million IU of sodium or calcium heparin in water to obtain 40 liters of solution.

Syringes are prefilled with the solution as follows:

Four typical heparin solutions which the syringe is ideally suited to dispense are the following:

1. Ampule syringe prefilled with 0.2 ml of a concentrated solution of sodium heparin of 25,000 IU/ml, thus 5,000 IU;

2. Ampule syringe prefilled with 0.2 ml of a concentrated solution of calcium heparin of 25,000 IU/ml of a concentration of 6%, thus 5,000 IU;

3. Ampule syringe prefilled with 0.3 ml of a concentrated solution of calcium heparin of 25,000 IU/ml having a concentration of calcium of 9%, thus 7,500 IU;

4. Ampule syringe prefilled with 0.4 ml of a 10% calcium heparin of 25,000 IU/ml, thus the syringe containing 10,000 IU.

The syringe may be made of glass or other suitable material which is insert to the drug solution. The hollow barrel is preferably of a size of about 0.55 to about 0.30 mm in diameter.

Supplementing the above description of the device of the invention, the following aspects are noteworthy. These may have been already described above or are inherent and are thus readily derivable therefrom.

The non-reusable prefilled syringes of the invention are ideally adapted for the standardization of anti-thrombic and/or anti-coagulant treatment to which patients are submitted. Indeed, the syringes allow high degree of precision in dosage, in the quantity administered by the injection, and the non-reuse of the syringe, all this while permitting a vein test to be undertaken prior to administration.

The increased precision in dosage is obtained due to the following factors. The slender diameter of the body of the syringe diminishes the size of the air bubble to being virtually non-existant and thus no longer needs to be ejected before injection. This ejection is frequently the cause of a certain loss of liquid. Furthermore, due to the slender diameter, the variation in the volume within the body of the syringe result in greater variation in the height of the column of liquid, which allows for a more precise measurement of the volume of liquid in the syringe.

The syringe of the invention is self-injectable. This precision in filling the disposable, self-injectable syringe allows for the maintenance of a regular and constant dosage, avoiding both over- and under-doses which might require surveillance and biological blood control.

The connection of the piston and the joint contributes by the presence of peripheral, concentric ribs to maintain a water-tight seal (despite the slender diameter of the tube) between the thin inner diameter of the piston and the interior end of the shaft of the piston, and by its truncated shape, which permits total expulsion of the liquid contained in the syringe, this contributing to the precision of the dose administered and avoids an under-dose.

The high degree of precision of the injection also is contributed by the needle which due to its small diameter and short length allows for the maximum precision and safety in a true subcutaneous injection. In effect, the preferred needles used with the pre-filled syringes of the invention, have a diameter of approximately 0.45 angstroms to about 0.50 mm and a preferred approximate length of 10 to about 15 mm. Such diameters limit the possibility of hematomas at the site of injection and the reduced length of the needle enhances the safety of administration. Moreover, the reduced length allows, in effect, subcutaneous injections to be administered perpendicularly to the surface of the skin by people who are not trained in giving injections—like the patients themselves—thus reducing to a minimum the possibility of error by puncturing a vein or a muscle.

It is to be noted that subcutaneous injection is essential to assure the slow diffusion of the drug which assures the efficacy of the injected dosage during the periods of 12 to 24 hours described above. One of the fundamental reasons for diffusion of the drug being spread out over that time, resides in the concentration of the drug solution, the importance of which should be emphasized.

Furthermore, it is advantageous that the needle is not mounted in the conventional way on the body of the syringe, but is fixed into the lower part of the latter in close proximity of the cylinder with the aid of, for example, an epoxy resin. Such a fixation on this slender diameter syringe presents in comparison with conventional mounted needles, an important advantage. In the case of a needle mounted on the base of the body of the syringe, significant dead space remains between the base of chamber 28 of the body of the cylinder and the lower end of part 24 of the latter. Such dead space normally causes risks of imprecision in the dose injected and often requires, in consequence, an overdose of the quantity contained in the body of the syringe in order to lessen the degree of such imprecision.

In contrast to such conventional practice, the fixation of the needle into the interior of end 24 of body 30 of the syringe allows the needle to be more deeply placed in the body of the syringe, thus reducing the amount of dead space. As a result, one avoids leaving residual quantities of the solution in the syringe and the necessity of an overdose, thus contributing to assuring the exactness and consistent precision of the dose injected.

It results from the foregoing description that the slender diameter and the reduced length of the needle make possible a subcutaneous injection with virtually complete security; moreover, the mode of fixation of the needle to the inside of the body of the syringe, together with the slender diameter of the body of the syringe and the structure of the stopper, contribute to avoiding overdoses and to assuring the precision of the dosage administered.

As described above, an important aspect of the invention is the non-reuse of the prefilled syringes. This is due to the combination of stopper 36 (having the particular structure described) together with shaft 52 of the piston of the syringe. The shaft has an extremity 56 which has a zone 58 with a diameter perceptibly smaller than the diameter of the aforementioned shaft and terminates with a flanged tip 60. These parts 58/60 work to act with stopper 36 to prevent the reuse of the syringes in conformance with the invention.

It may also be noted that the reduction of dead space in the interior part of the syringe body due to the fixation of the needle in to the interior of the latter, cooperates with assembly 58/60 of the shaft, which is provided in recess 42 of stopper 36 to prevent reuse. In effect, by doing away with such dead space, the adherence of the entire surface of the piston stopper to the body of the syringe augments the necessary force for the eventual reaspiration of a liquid, contributing to prevent reuse.

Furthermore, by exercising a weak force of traction of very short duration on the shaft assembly of the piston stopper in order to achieve the vein test, the piston stopper in the elastic material can exercise the proper resistance on the aforementioned assembly without which it could come apart during the vein test.

Thus, in accordance with the invention there is obtained prefilled, non-reusable syringes which permit the administration of calculated doses with precision. In effect, because of coaction of the constituent elements of the syringes of the invention, a fixed needle assembly, stopper, and slender diameter, residual quantities of the solution do not remain in the syringe and it is not necessary to give overdoses of the quantities contained in said syringe. The cooperation between the elements mentioned permits the standardization of anti-thrombic and/or anti-coagulant treatment for the following reasons:

The dose contained in the syringe is exactly calculated and is entirely injected. The exactness of the dose administered facilitates treatment, avoiding all risk of hemorrhage which might result from an overdose and allowing the maintenance of regular and constant dosages—avoiding both underdoses and overdoses which might require surveillance and biological blood control.

A true subcutaneous injection is achieved, i.e., the injected dose is administered with complete security, whoever gives the injection, thus practically eliminating the risk of hematomas due to punctures and errors in placing the injection, due to the choice of a needle of slender diameter and reduced length.

The structure of the prefilled syringes allow vein tests to be taken by controlling the placement of the injection and assures that one is not in a vein—this resulting as described from the coaction of shaft 58 and end 60 in stopper 36. The vein test combined with the use of a needle of reduced length, assure that the diffusion of the heparin solution or heparin salt contained in the syringe will be diffused slowly (delayed diffusion) in accordance with the conditions required by the treatment.

Moreover, the structure of the stopper and described assembly is such that the relationship between the resistance of the rubber which constitutes the stopper and the shape of tip 60 allows for the limited force of withdrawal which suffices for a vein test (enough suction to withdraw blood from a vein if the needle is accidentally placed on the wrong spot), while being less than the force required for the reaspiration of new liquid after use. This assures the impossibility of reusing the syringes under undesirable conditions.

Moreover, the number of manipulations required for an injection is reduced since one disposes of a prefilled syringe with a fixed needle which can be used without any preparation.

The described invention provides a convenient and most reliable device and method for self-administration of a drug without reuse. The syringe was developed with a familiarity and for conformance with the requirements of the medical profession. The syringe is a device which has been constructed to function in close association with and taking into consideration the physiological conditions of the patient. The construction of the head of the piston is such that there is a close approximation or equilibrium between the withdrawal force necessary to pull the piston back with the cylinder when taking the vein test and the blood pressure of a patient. Thus the syringe's elements do not only coact with themselves, as described herein, but coact also with the physiological conditions of a patient. This is believed to be another of these rather few examples of a medical device whose operative parts are adapted to be capable of fulfilling a required function while coating with a living organism. The invention is not limited to the particular embodiment except as called for in the following claims.

We claim:

1. In a syringe, adapted to preclude reuse, prefilled with a drug solution, having a hollow syringe barrel with an open distal end adapted to have a needle fixed thereto in fluid communication therewith for dispensing of the drug solution contained therein through the needle, the syringe having an open rear end adapted to be sealed by an elastomeric stopper in sliding engagement with the walls of the syringe barrel, the improvement which comprises a plunger assembly including a plunger-rod having a projection at one end, the projection comprising a reduced diameter portion terminating in a flanged tip, and the elastomeric stopper having a recess in one end thereof, the recess terminating in an enlarged flange receiving portion, wherein the diameter of the flanged tip of the projection of the rod is less than the diameter of the flange receiving portion of the recess of the stopper but greater than the diameter of the recess of the stopper, the interengaging surfaces of which are configured for releasably making engagement, and a drug solution contained within the syringe, wherein the plunger assembly is adapted so that the stopper is not released from the projection of the rod when limited manual withdrawal of the plunger is performed when the syringe is filled with the solution, for a vein test prior to administration of the solution of the drug to be administered, and the stopper is disconnected from the rod, remaining in the barrel, when, after the drug has been administered, and the syringe is empty, the plunger is withdrawn within the barrel with a force equal to that necessary to aspirate a new drug solution into the syringe, thereby rendering the syringe useless for reuse.

2. The syringe of claim 1 wherein the stopper is disconnected from the rod when, after the drug has been administered, the plunger is withdrawn within the barrel with a force greater than that necessary to aspirate a new solution into the syringe.

3. The syringe of claim 1 wherein the barrel is of a size capable of containing a 0.2 to 0.4 ml dose of the drug solution.

4. The syringe of claim 3 wherein the dosage is 5000 IU or 2500 IU.

5. The syringe of claim 3 wherein the drug solution is a heparin salt.

6. In a syringe, adapted to preclude reuse, pre-filled with a drug solution, having a hollow syringe barrel with an open distal end adapted to have a needle fixed thereto in fluid communication therewith for dispensing of the drug solution contained therein through the needle, the syringe having an open rear end adapted to be sealed by an elastomeric stopper in sliding engagement with the walls of the syringe barrel, the improvement which comprises a plunger assembly including a plunger-rod having a projection at one end, the projection comprising a reduced diameter portion terminating in a flanged tip, and the elastomeric stopper having a recess in one end thereof, the recess terminating in an enlarged flange receiving portion, wherein the diameter of the flanged tip of the projection of the rod is less than the diameter of the flange receiving portion of the recess of the stopper but greater than the diameter of the recess of the stopper, the interengaging surfaces of which are configured for releasably making engagement, so that the stopper is not released from the projection of the rod when limited manual withdrawal of the plunger is performed for a vein test prior to administration of the solution of the drug to be administered, and the stopper is disconnected from the rod, remaining in the barrel, when, after the drug has been administered, the plunger is withdrawn within the barrel with a force equal to that necessary to aspirate a new solution into the syringe, thereby rendering the syringe useless for reuse.

7. The syringe of claim 6 wherein the flanged tip at the end of the projection of the rod is frustoconical.

8. The syringe of claim 6 wherein at least one end of the stopper is a closed end.

9. The syringe of claim 6 wherein the stopper has ribs which cooperate with the side of the barrel to seal the drug solution in the barrel.

10. The syringe of claim 6 wherein the stopper has a non-planar surface in contact with the drug solution.

11. The syringe of claim 10 wherein the non-planar surface is conical in shape.

12. The syringe of claim 11 wherein the conical surface of the stopper is essentially non-distorting.

13. The syringe of claim 6 wherein the edge of the stopper which is in contact with the drug solution is convex.

14. The syringe of claim 13 wherein the contacting edge of the stopper is adapted to maintain its convex shape during retraction of the plunger for the vein test.

15. The syringe of claim 7 wherein the terminating end of the enlarged flange receiving portion of the stopper is conical.

16. The syringe of claim 15 wherein the frustoconical tip of the projection of the plunger-rod contacts the conical portion of the surface of the recess at selected portions only.

17. The syringe of claim 16 wherein the frustoconical tip of the projection of the plunger-rod does not contact the apex of the conical surface portion of the recess.

18. The syringe of claim 16 wherein only the oblique face of the frustoconical tip contacts the conical surface portion of the recess of the stopper.

19. The syringe of claim 18 wherein the only portions of the projection of the plunger rod which contact the surfaces of the recess of the stopper are along the oblique face of the frustoconical tip.

20. The syringe of claim 16 wherein the end of the stopper which contacts the plunger-rod is annularly separated from the barrel of the syringe.

21. The syringe of claim 6 wherein the end of the stopper which contacts the plunger-rod is annularly separated from the barrel of the syringe.

22. The syringe of claim 9 wherein the barrel and the stopper are annularly separated from each other at more than two locations.

23. The syringe of claim 22 wherein the surfaces of the stopper along those areas of the stopper which are annularly separated from the barel are non-linear.

24. The syringe of claim 9 wherein the forwardmost end of the projection of the plunger-rod terminates at a position before that of the forwardmost rib of the stopper.

25. The syringe of claim 6 wherein the stopper is a solid, unitary structure.

26. In a syringe, adapted to preclude reuse, prefilled with a heparin salt solution, having a hollow syringe barrel with an open distal end adapted to have a needle fixed thereto in fluid communication therewith for dispensing of the drug solution contained therein through the needle, the syringe having an open rear end adapted to be sealed by an elastomeric stopper in sliding engagement with the walls of the syringe barrel, the improvement which comprises a plunger assembly including a plunger-rod having a projection at one end, the projection comprising a reduced diameter portion terminating in a frustoconical tip, and the elastomeric stopper, which is a solid, unitary structure, having a recess in one end thereof, the recess extending into an enlarged tip receiving portion, the terminating end of which is conical, wherein the diameter of the frustoconical tip of the projection of the rod is less than the diameter of the tip receiving portion of the recess of the stopper but greater than the diameter of the recess of the stopper, wherein the frustoconical tip of the projection of the plunger-rod and the conical portion of the surface of the recess of the stopper are configured so that the truncated portion of the frustoconical tip does not contact the apex of the conical surface portion of the recess, and so that the oblique portions of the frustoconical tip do contact the conical surface portion of the recess, wherein the stopper has ribs which cooperate with the sides of the barrel of the syringe to seal the drug solution in the barrel, the ribs being separated by areas which are annularly spaced away from the barrel of the syringe, the surfaces of the annular separations along the stopper being non-linear, and the end of the stopper which contacts the plunger-rod being annularly separated from the barrel of the syringe, and wherein the interengaging surfaces of the stopper and the projection of the plunger-rod are configured so that, the stopper is not released from the projection of the rod when limited manual withdrawal of the plunger is performed for a vein test prior to administration of the solution of the drug to be administered, and the stopper is disconnected from the rod, remaining in the barrel, when, after the drug has been administered, the plunger is withdrawn within the barrel with a force equal to that necessary to aspirate a new solution into the syringe, thereby rendering the syringe useless for reuse.

27. The syringe of claim 26 wherein the needle is fixed inside the forward portion in close proximity to the cylinder of the syringe, thus reducing the dead space and contributing to more precise administration of the drug.

28. The syringe of claim 27 wherein the needle has a length of about 10 to 15 mm.

29. The syringe of claim 28 wherein the needle has a diameter of about 0.45 to 0.50 angstroms.

30. In a syringe, adapted to preclude reuse, prefilled with a drug solution, having a hollow syringe barrel with an open distal end adapted to have a needle fixed thereto in fluid communication therewith for dispensing of the drug solution contained therein through the needle, the syringe having an open rear end adapted to be sealed by an elastomeric stopper in sliding engagement with the walls of the syringe barrel, the improvement which comprises a plunger assembly including a plunger-rod having a projection at one end, and the elastomeric stopper having a recess in one end thereof, and means for releasably engaging the stopper and the projection of the plunger-rod, so that the stopper is not released from the projection of the rod when there is performed a vein test prior to administration of the solution of the drug to be administered, and so that the stopper must disconnect from the rod, remaining in the barrel, whenever, after the drug has been administered, the plunger is withdrawn within the barrel to aspirate a new solution into the syringe, thereby rendering the syringe useless for reuse, wherein the engaging means comprises the projection of the plunger-rod and the recess of the stopper wherein the projection of the plunger-rod has a reduced diameter portion which terminates in a frustoconical tip, the recess of the stopper, which stopper is solid and unitary, extends into an enlarged tip receiving portion, the terminating end of which is conical, and wherein the diameter of the frustoconical tip of the projection of the rod is less than the diameter of the tip receiving portion of the recess of the stopper but greater than the diameter of the recess of the stopper, and wherein the frustoconical tip of the projection of the plunger-rod and the conical portion of the surface of the recess of the stopper are configured so that the truncated portion of the frustoconical tip does not contact the apex of the conical surface portion of the recess, and so that the oblique portions of the frustoconical tip do contact the conical surface portion of the recess.

31. A method for administering once a preselected mini-dose of a solution of heparin salt with a syringe, adapted to preclude reuse, the syringe having a hollow syringe barrel with an open distal end adapted to have a needle fixed thereto in fluid communication therewith for dispensing of the drug solution contained therein through the needle, an open rear end adapted to be sealed by an elastomeric stopper in sliding engagement with the walls of the syringe barrel, and a plunger assembly including a plunger-rod having a projection at one end, the projection comprising a reduced diameter portion terminating in a flanged tip, and the elastomeric stopper having a recess in one end thereof, the recess terminating in an enlarged flange receiving portion, wherein the diameter of the flanged tip of the projection of the rod is less than the diameter of the flange receiving portion of the recess of the stopper but greater than the diameter of the recess of the stopper, the interengaging surfaces of which are configured for releasably making engagement, so that the stopper is not released from the projection of the rod when limited manual withdrawal of the plunger is performed when the syringe is filled with the solution, for a vein test prior to administration of the solution of the drug to be administered, and the stopper is disconnected from the rod, remaining in the barrel, when the plunger is withdrawn within the barrel when the syringe is empty, after the drug has been administered, in an attempt to aspirate a new solution into the syringe, which method comprises:

administering the solution contained in the full syringe subcutaneously to the patient, and thereafter attempting to withdraw the plunger assembly within the barrel for aspiration of a new solution into the empty syringe, while simultaneously, disconnecting the stopper from the projection of the plunger-rod, whereby the stopper is disconnected from the plunger-rod rendering the syringe useless for reuse.

32. The method of claim 30 wherein the drug administered to the patient is a heparin salt, the dosage of which is about 2500 IU to 10,000 IU.

33. The method of claim 32 wherein the dosage is 5,000 IU.

34. The method of claim 30 which further comprises performing a vein test prior to administering the solution contained in the full syringe by manually, slightly withdrawing the plunger within the barrel of the syringe, the stopper remaining attached to the plunger, and determining whether blood has thereby been aspirated into the distal end of the syringe.

35. The method of claim 30 which further comprises administering the minidose of heparin to the patient at preselected times preceeding surgery without requiring the intervention of trained medical personnel, whereby a person without medical training may perform presurgical preparation.

36. The method of claim 30 which further comprises withdrawing the plunger from the barrel and separately disposing of the plunger, whereby the stopper remains in the barrel of the syringe thus preventing reuse.

* * * * *